United States Patent [19]

Dreyfuss et al.

[11] Patent Number: 5,116,816
[45] Date of Patent: May 26, 1992

[54] CYCLOSPORIN PEPTOLIDES HAVING AN α-HYDROXYCARBOXYLIC ACID AT POSITION 8

[75] Inventors: Michael M. Dreyfuss; Max H. Schreier, both of Basel; Hans Tscherter, Allschwil; all of Switzerland

[73] Assignee: Sandoz Ltd., Basel, Switzerland

[21] Appl. No.: 209,680

[22] Filed: Jun. 20, 1988

[30] Foreign Application Priority Data

Jun. 19, 1987 [CH] Switzerland .......... 2317/87
Jul. 2, 1987 [CH] Switzerland .......... 2517/87

[51] Int. Cl.$^5$ .......... A61K 37/02; C07K 7/50; C07K 7/54; C07K 11/02
[52] U.S. Cl. .......... 514/11; 514/885; 530/317; 530/323; 530/335; 530/338; 530/345; 435/71.1; 435/254
[58] Field of Search .......... 530/323, 317; 514/9, 514/11, 885

[56] References Cited

U.S. PATENT DOCUMENTS

| | | | |
|---|---|---|---|
| 4,220,641 | 9/1980 | Traber et al. | 514/11 |
| 4,384,996 | 5/1983 | Bollinger et al. | 530/321 |
| 4,649,047 | 3/1987 | Kaswan | 514/11 |

OTHER PUBLICATIONS

Rudinger, Peptide Hormones, Parsons (Ed.), U. Park Press, Baltimore, pp. 1-7 (1976).
Twentyman et al., Br. J. Cancer, vol. 56, pp. 55-57 (1987).

*Primary Examiner*—Christina Chan
*Attorney, Agent, or Firm*—Gerald D. Sharkin; Robert S. Honor; Thomas O. McGovern

[57] ABSTRACT

Cyclic peptolides having the structure of a cyclosporin in which one amide linkage is replaced by an ester linkage are obtained by fermentation of fungal strains of the genus Cylindrotrichum Bonorden, or by cyclization of a hydroxy-undecapeptide. The cyclic peptolides have immunosuppressive, anti-inflammatory and anti-parasitic properties.

9 Claims, No Drawings

CYCLOSPORIN PEPTOLIDES HAVING AN α-HYDROXYCARBOXYLIC ACID AT POSITION 8

This invention relates to novel cyclic peptolides useful as pharmaceuticals.

The term peptolide is used herein to mean a natural or synthetic compound consisting of α-hydroxy and α-amino acids joined together by both amide and ester linkages. Thus the structure obtained by replacing an amide linkage by an ester linkage in a peptide is a peptolide.

An important class of peptides is the cyclosporins, which are characterised by a cyclic structure, normally comprising 11 amino acid residues, one of which is the N-Methyl-(4R)-4-but-2E-en-1-yl-4-methyl-(L)-threonyl residue, designated MeBmt, or a derivative thereof. Many cyclosporins have pharmacological properties, particularly immunosuppressive and antiinflammatory properties. The first cyclosporin to be isolated was the naturally occurring fungal metabolite cyclosporin A, (Ciclosporin) sold commercially under the registered Trade Mark Sand Immune ®. This compound has the structure indicated in formula I

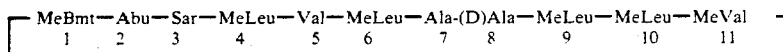

(For a complete list of abbreviations used herein, see Table II)

By convention, the amino-acid residues of cyclosporins are have the (L) configuration unless otherwise shown; thus in formula I the alanine at position 8 has the (D) configuration. The symbol Me before the abbreviation for an amino acid signifies that the amino acid residue is N-methylated on the nitrogen in the amide linkage.

The present invention provides a cyclic peptolide which has the structure of a cyclosporin in which one amide linkage is replaced by an ester linkage.

Preferably the cyclic peptolide is composed of one MeBmt residue or a derivative thereof, 9 other α-amino acid residues and one α-hydroxyacid residue, which is preferably located at position 8.

Preferred derivatives of MeBmt are the 8'hydroxy derivative (8'-OHMeBmt) and the saturated dihydro derivative MeBmtH₂, having the structures shown below:

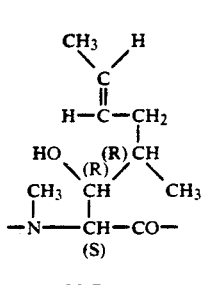

MeBmt

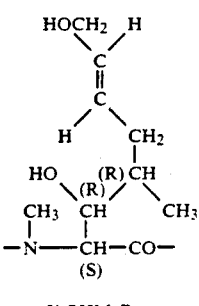

8'-OHMeBmt

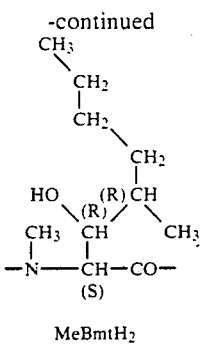

MeBmtH₂

The preferred cyclic peptolides according to the invention have the structure shown in formula II

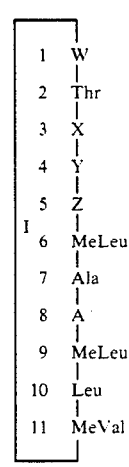

II in which
W is MeBmt, 8'-OHMeBmt or MeBmtH₂,
X is Sar or Gly,
Y is MeLeu or Leu,
Z is Leu, Ile or Val,
and A is the residue of an α-hydroxycarboxylic acid, preferably of formula III

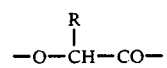

III in which R is $C_{1-4}$ alkyl.

More preferably in formula III R is isopropyl, so that A represents

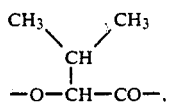

the residue of α-hydroxy isovaleric acid, abbreviated Hiv. The most preferred compound according to the invention is that in which, in formula II, W is MeBmt, X is Sar, Y is MeLeu, Z is Leu, and A is (D)Hiv. This may be represented by the full structural formula shown in formula IV

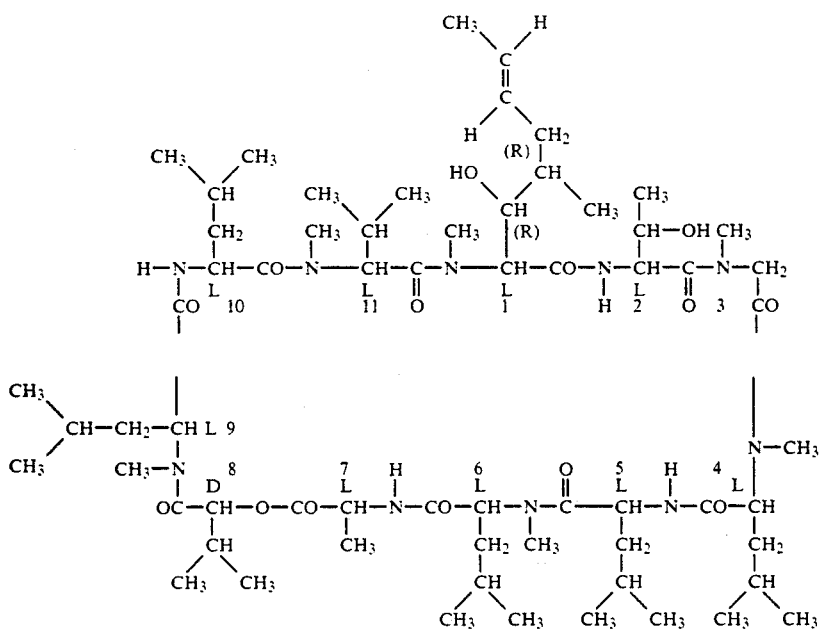

or by using the now conventional nomenclature for cyclosporins, based upon the structure of Ciclosporin (cyclosporin A) shown in formula I. This is done by listing in order each residue in the molecule which differs from that found in Ciclosporin, and adding the term "Ciclosporin". Thus the compound of formula IV may be represented as (Thr)²(Leu)⁵(D-Hiv)⁸(Leu)¹⁰-Ciclosporin.

that is, Ciclosporin in which Thr replaces Abu in position 2, Leu replaces Val in position 5, (D)Hiv replaces (D)Ala in position 8 and Leu replaces MeLeu in position 10, the other residues being identical with those in Ciclosporin.

The cyclic peptides according to the invention may be produced by cultivating a producing microorganism strain in a nutrient medium. Preferred microorganisms are fungal strains of the genus Cylindrotrichum Bonorden, in particular the strain NRRL 18230, which produces cyclic peptolides of formula II.

The strain has been isolated from a leaf sample from Waldenburg in the Swiss Jura, and a viable culture of the strain was deposited on Jun. 17, 1987 at the US Department of Agriculture (North Central Region, Northern Regional Research Centre), Peoria, Ill. and was given the reference number NRRL 18230. The culture may also be obtained from Sandoz Ltd., Basle, Switzerland.

The fungal strain NRRRL 18230 is a hyphomycete and when incubated at 21°-24° C. on 2% malt extract/agar (=MA; 2% malt extract, 0.4% yeast extract, 2% agar in demineralized water) produces aseptate or frequently 1-septate bacilliform hyaline conidia, 6–15μ×1-.5–2.7μ (mostly 9.5–13.5μ) large.

The conidiogenic cells are generally cylindrical and have a conspicuous colarette; some cells appear sympodial-polyphialidic. According to the identification key of M. B. Elles (Dematiaceous Hyphomycetes; Commonwealth Mycological Institute, Kew, Surrey, England, 1971), the strain may best be classified in the genus Cylindrotrichum Bonorden.

The fungal strain NRRL 18230 grows relatively slowly and after 10 days incubation at a temperature of 21° C. forms colonies of 4-7 mm diameter with a velvety grey aerial mycelium. The optimum growth temperature is between 18° C. and 27° C., and above 33° C. no growth occurs. The branched and septate aerial mycelium of colonies cultivated on MA at 21° C. is generally 1.5–3.5μ (usually 2–3μ) wide; in the substrate mycelium hyphae of up to 5.5μ width can be observed.

The invention also provides fermentation broths obtained by cultivation of a strain of the fungal genus Cylindrotrichum Bonorden. The novel strain NRRL 18230 may be cultivated by an aerobic surface or immersion process at suitable temperature in a variety of nutrient media containing the nutrients and minerals in usuable form.

Thus, the medium should contain an assimilatable source of carbon and optionally mineral salts and growth factors. All of these constituents may be added in the form of well-defined simple compounds or in the form of complex mixtures obtained from biological sources. Cultivation is carried out according to conventional methods, and the cyclic peptolides formed during the fermentation may finally be isolated from the culture medium by the use of known chromatographic methods. The cyclic peptolides of the invention may also be obtained by the cultivation of variant or mutant strains obtained by selection or by the effect of mutation-inducing agents e.g. U.V. light, X-rays or chemical mutagens on NRRL 18230 or other strains of Cylindrotrichum Bonorden.

The cyclic peptolides of the present invention may also be prepared by synthetic or semi-synthetic methods, for example by the cyclisation of a linear peptolide or a linear peptide having an —OH terminal group in place of an —NH₂ terminal; or by the replacement of an amide linkage in a natural, synthetic or semi-synthetic cyclosporin with an ester linkage.

The total synthesis of the preferred compounds of formula II may be carried out in a manner analogous to the total synthesis of cyclosporin A and analogues as described for example in European Patent 34 567 or by R. Wenger in Transplantation Proceedings, vol. XV pp. 2230-2241 (1983). According to this method the C-protected heptapeptide having the formula V

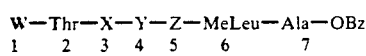
$$\text{W—Thr—X—Y—Z—MeLeu—Ala—OBz} \quad \text{V}$$
$$\quad 1 \quad 2 \quad 3 \quad 4 \quad 5 \quad\quad 6 \quad\quad 7$$

in which Bz is the benzyl group and W, X, Y and Z are as defined above is first prepared, and this is then reacted with a tetrapeptide corresponding to the sequence 8 through 11.

This tetrapeptide, of formula VI

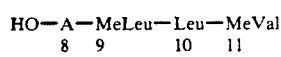
$$\text{HO—A—MeLeu—Leu—MeVal} \quad \text{VI}$$
$$\quad\quad 8 \quad\quad 9 \quad\quad 10 \quad 11$$

contains three normal peptide bonds, but has an O-terminal in place of an N-terminal since the residue at position 8 is derived from an α-hydroxy acid rather than from an α-aminoacid.

The tetrapeptide may be prepared according to the scheme shown in the following flow sheet:

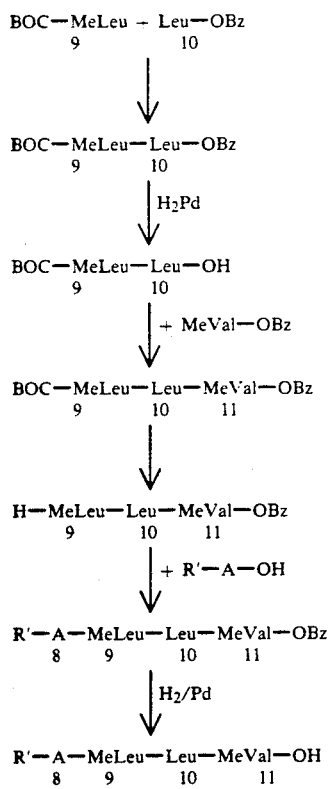

in which BOC is the N-protecting group t-butyloxycarbonyl and R' is a suitable O-protecting group. Thus the reagent represented above as R'—A—OH is an OH-protected α-hydroxycarboxylic acid, which when A is of formula III, has the formula VII

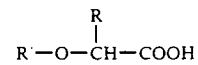
$$\begin{array}{c} R \\ | \\ R'\text{—O—CH—COOH} \end{array} \quad \text{VII}$$

where R is as defined above.

Preferably the group R' is selected from the groups

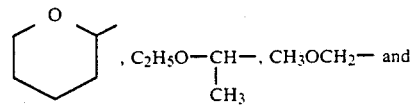

, $C_2H_5O-\underset{\underset{CH_3}{|}}{CH}-$, $CH_3OCH_2-$ and tBuSi(CH$_3$)$_2$—. The preferred compounds of formula VII may be obtained by reacting the α-hydroxy acid, in carbonyl-protected from, e.g. as the benzyl ester, with dihydrofuran, ethoxyethylene, t-butyldimethylchlorosilane or chlorodimethyl ether respectively.

Reaction of the COOH-protected heptapeptide V with the hydroxy tetrapeptide VI, in OH protected form, gives rise to a linear hydroxy undecapeptide of formula VII having the sequence 8 through 7.

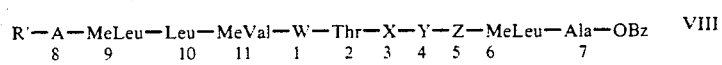
$$\text{R'—A—MeLeu—Leu—MeVal—W—Thr—X—Y—Z—MeLeu—Ala—OBz} \quad \text{VIII}$$
$$\quad\quad 8 \quad\quad 9 \quad\quad 10 \quad\quad 11 \quad 1 \quad 2 \quad 3 \quad 4 \quad 5 \quad\quad 6 \quad\quad 7$$

Finally cyclisation of this linear hydroxypeptide may be carried out by removing the protecting groups by acidic and basic hydrolysis and coupling residue 8 to 7 with the formation of an ester linkage. The coupling reaction is preferably carried out in methylene chloride using a carbodiimide reagent for example N-ethyl-N'-(3-dimethylamino)propyl carbodiimide.

The heptapeptide of formula V and the tetrapeptide of formula VI may also be obtained by controlled hydrolysis of cyclic peptolides of formula II obtained from fermentation. This treatment with trifluoroacetic acid at low temperature cleaves the bond between residues 11 and 1 to give a linear undecapeptolide containing residues 1 (N-terminal) through 11 (C-terminal), with an ester linkage at 7-8. Alkaline hydrolysis gives the 1-7 heptapeptide and the 8-11 hydroxytetrapeptide. Semisynthetic cyclic peptolides may then be produced for example by reacting the hydroxytetrapeptide produced in this way with a synthetic heptapeptide, or vice versa, and cyclising the linear product.

For the purposes of the cyclisation reaction the peptide may if desired be in O-protected form, that is, the hydroxy groups in the 1-MeBmt or derivative thereof, and/or in the 2-threonine residue may bear protecting groups, as described in European Patent 34 567. Such O-protecting groups are then removed subsequent to ring closure by standard methods. Removal of for example a benzyl group by hydrogenation will also lead to the hydrogenation of MeBmt to MeBmtH$_2$, and in any case initially-produced cyclic peptolides containing a MeBmt residue at position 1 may be converted to the corresponding MeBmtH$_2$ compound by hydrogenation.

Accordingly the invention provides a process for the production of a cyclic peptolide of formula II, stated above, which process comprises a) removing the O-protecting groups from a cyclic peptolide of formula II in O-protected form;

b) cyclising a straight chain hydroxy-endecapeptide of formula VIII, in unprotected form or O-protected on one or both of residues 1 and 2, and, when required, carrying out process step (a); and, when desired c) hydrogenating a cyclic peptolide of formula II thus obtained wherein W is MeBmt to obtain the corresponding cyclic peptolide wherein W is MeBmtH$_2$.

The cyclic peptolides of the invention exhibit pharmacological activity and are, therefore, useful as pharmaceuticals. In particular, the compounds show immunosuppressant, anti-inflammatory and anti-parasitic activity in the following tests:

IN VITRO MODELS (1-3)

1. Interleukin 2 (IL-2) inhibition

Interleukin 2 is induced by mitogen stimulation of mouse spleen cells. Forty eight hour supernatants are collected and assayed for their content of IL-2 by use of a IL-2-dependent cell line (CTLL). The growth of these cells is assayed after 48 hours by use of an enzymatic assay which measures mitochondrial activity.

[T. Mosmann J. Immunol. Methods 65:55-63 (1983)]

The compounds of the invention have an inhibitory effect at concentrations from IC$_{50}$ 0.01 to approx. 0.1 ug/ml.

2. Proliferative Response of Lymphocytes to Allogeneic Stimulation

Murine Mixed Lymphocyte Reaction (MLR)

Spleen cells ($0.5 \times 10^6$) from Balb/c mice (female, 8-10 weeks) are co-incubated for 5 days with $0.5 \times 10^6$ irradiated (2000 rads) or mitomycin C treated spleen cells from CBA mice (female, 8-10 weeks). The irradiated allogeneic cells induce a proliferative response in the Balb c spleen cells which can be measured by labeled precursor incorporation into the DNA. Since the stimulator cells are irradiated (or mitomycin C treated) they do not respond to the Balb/c cells with proliferation but do retain their antigenicity.

[T. Meo "Immunological Methods", L. Lefkovits and B. Pernis, Eds., Academic Press, N.Y. pp. 227-239 (1979)]

The compounds of the invention have an inhibitory effect at concentrations of from IC$_{50}$ = 0.0001 to approx. 0.001 ug/ml.

3. Primary Humoral Immune Response to Sheep Red Blood Cells in vitro (Mishell-Dutton Assay)

Mouse spleen cells (OFI, female, 8-10 weeks, $1 \times 10^7$) are co-cultured with sheep erythrocytes (SRBC, $3 \times 10^7$) for 3 days in 1 ml final volume in 24 well plates. Lymphocytes are harvested, washed and plated at a density of $1 \times 10^6$ cells onto soft agar with fresh antigen (SRBC). Complement (guinea pig serum) is added after a 60-90 minute incubation period and incubation is continued for another 60 minutes after which the test is evaluated by counting the plaques under the microscope. During the 3 day incubation, the lymphocytes are sensitized to the antigen (SRBC). When incubated with antigen again, B-lymphocytes secrete specific antibody which binds to the antigen in the vicinity of the secretory lymphocyte. Addition of complement causes lysis of the antibody-coated erythrocytes yielding a plaque. Each plaque represents a single antibody-producing cell.

[R. I. Mishell & R. W. Dutton J. Exp. Med. 126:423-442 (1967)]

The suppression of plaque-forming cells is observed at concentrations of compound according to the invention of from IC$_{50}$ 0.01 to approx. 0.1 ug/ml.

IN VIVO MODELS (4-9)

4. Formation of plaque forming cells (humoral immune response)

Female rats (OFA) are immunised by the i.v. injection of ($1 \times 10^8$) sheep erythrocytes (SRBC) and treated on three consecutive days with the drugs under investigation. Spleen cell suspensions are prepared 6 days after immunisation and $1 \times 10^6$ lympocytes are plated onto soft agar in the presence of indicator cells (SRBC) and complement. Lysis of the indicator cells due to secretion of specific antibody and presence of complement yields plaques. The number of plaques per plate are counted and corrected for the number of plaques per spleen.

[N. K. Jerne & A. A. Nordin Science 140:405 (1969); N. K. Jerne, A. A. Nordin & C. Henry (1963) In: "Cell Bound Antibodies", B. Amos & H. Koprowski, Eds., Wistar Inst. Press, Philadelphia pp. 109-125 (1963)].

The compounds according to the invention produce this effect in the rat when given orally at an ED$_{50}$ of approx. 6.0-8.0 mg/kg.

5. Localised graft-versus-host-reaction

Spleen cells ($1 \times 10^7$) from 6 week old female Wistar/Furth (WF) rats are injected subcutaneously on day 0 into the left hind-paw of female (F344 $\times$ WF)FI rats weighing about 100 g. Animals are treated for 4 consecutive days and the popliteal lymph nodes are removed and weighed on day 7. The difference in weight between the two lymph nodes is taken as the parameter for evaluating the reaction.

[W. L. Ford, W. Burr & M. Simonsen Transplantation 10:258-266 (1970)]

The compounds of the invention have an oral ED$_{50}$ in this test of approx. 20-30 mg/kg.

6. Freund's Adjuvant Arthritis

OFA and Wistar rats (male or female, 150 g body weight) are injected i.c. at the base of the tail or in the hind paw with 0.1 ml of mineral oil containing 0.6 mg of lyophilized heat-killed Mycobacterium smegmatis. Treatment is started on day 14, when the secondary inflammation is well developed (days 14-20). At the end of the experiment, the swelling of the joints is measured by means of a micro-caliper. ED$_{50}$ is the oral dose in mg/kg orally which reduces the swelling (primary or secondary) to half of that of the controls. For the compounds of the invention the oral ED$_{50}$ is up to 30 mg/kg.

[C. A. Winter & G. W. Nuss Arthritis and Rheumatism 9:394-404 (1966)]

7. Kidney allograft reaction in the rat

One kidney from a female Fisher 344 rat is transplanted onto the renal vessel of a unilaterally (left side) nephrectomized Wistar/Furth recipient rat using an end-to-end anastomosis. Ureteric anastomosis is also end-to-end. Treatment commences on the day of transplantation and is continued for 14 days. A contralateral nephrectomy is done seven days after transplantation, leaving the recipient relying on the performance of the donor kidney. Survival of the recipient is taken as the parameter for a functional graft.

[P. C. Hiestand, et al Immunology 55 249-255 (1985)]

The compounds of the invention are effective in the rat at an oral ED$_{50}$ of from 6 to approx. 9 mg/kg.

8. UV Erythema test

The test is carried out on female albino guinea pigs, approx. 150 g wt. The animals are shaved on both flanks using a Braun micro razor, without causing skin irritation. For each test substance five animals are subjected to a defined intensity of UV radiation for 10 seconds on each of four areas of skin (10 mm diameter). Immediately afterwards 50 microliters of a solution of the test substance in ethanol/propylene glycol/dimethylacetamide (19:19:2 v/v) is applied to two of the irradiated areas on each animal and 50 microliters of the solvent mixture to the other two as controls. Four hours after application, the degree of erythema is estimated visually.

[Raake, W. Arzneim.-Forsch. 34(I) No. 4 (1984)]

The compounds of the invention are effective at a concentration of from 1 to 10%.

9. Anti-malaria test

Mice (OFI, male) are infected i.p. on day 0 with 0.2 ml of a suspension of erythrocytes containing $10^7$ cells parasitized by Plasmodium berghei (Strain NK 65). The test substance is administered s.c. at varying dosages using 5 to 10 dose/mice. The survival time is recorded, and the minimum effective dose (MED) calculated by comparison of survival time with that for untreated controls. For controls, survival time is approx. 7 days. The MED is the dosage at which survival time is doubled.

[L. Rane in "Chemotherapy and Drug Resistance in Malaria, ed. W. Peters, Academic Press, New York, (1979)]

In view of their immunosuppressive activity, the compounds are therefore useful for the prophylaxis and treatment of conditions and diseases requiring a suppression of the immune response, for example in the treatment of autoimmune diseases, the prevention of tissue rejection in transplantation, e.g. bone marrow and kidney transplantation. Specific autoimmune diseases, for which the compounds of the invention may be used include aplastic anaemia, pure red cell anaemia, idiopathic thrombocytopenia, systemic lupus erythematosis, polychondritis, sceleroderma, Wegner's granulomatosis, dermatomyositis, chronic active hepatitis, myasthenia gravis, Steven-Johnson syndrome, psoriasis, idiopathic sprue, Crohn's disease, Graves' opthalmopathy, sarcoidosis, multiple sclerosis, primary biliary cirrhosis, primary juvenile diabetes, posterior uveitis, interstitial pulmonary fibrosis and psoriatic arthritis.

Because of their antiinflammatory properties the compounds of the invention are useful in the treatment of inflammatory conditions, particularly inflammatory states with an aetiology which includes an autoimmune component, for example the treatment of arthritis and rheumatic diseases such as chronic progressive arthritis.

In view of their anti-parasitic activity, the compounds are also useful for the treatment of parasitic disease, for example schistosomiasis, filariasis, leishmaniasis, coccidioidomycosis and, in particular, malaria.

The compounds of the invention are also useful in the treatment of certain skin diseases and conditions, which include, in addition to those already mentioned above, alopecia areata, urticaria, vasculitis, erythema, atopic dermatitis, eczema, cutanous eosinophilia and angioderma.

For these indications, the appropriate dosage will, of course, vary depending upon for example the compound employed, the host, the mode of administration and the nature and severity of the condition being treated. However, in general, satisfactory results in animals are indicated to be obtained at daily dosages from about 1 mg/kg to about 200 mg/kg body weight. In larger mammals, for example humans, an indicated daily dosage is in the range from about 70 to about 3000 mg of a compound according to the invention conveniently administered in divided doses up to four times a day.

The compounds of the invention may be administered by any conventional route, in particularly orally, for example in the form of tablets or capsules, parenterally in the form of injectable solutions or suspensions or topically in the form of a lotion, cream or gel.

The compound of Example 2 : $(Thr)^2$ $(Leu)^5$ $(D-Hiv)^8$ $(Leu)^{10}$-Ciclosporin is the preferred compound. It has, for example, been determined that this compound is effective at a concentration of 5% in the UV-erythema test in the mouse (test method 8 above) as compared to a concentration of 2.5% for indomethacin. It is therefore indicated that for topical use in treatment of inflammatory skin conditions, the compound of Example 2 may be administered to larger mammals, for example humans, by similar modes of administration at correspondingly higher dosages than conventionally employed with indomethacin.

It has also been determined that the compound of Example 2 has an $ED_{50}$ value of approx. 25 mg/kg in the treatment of localized graft versus host reaction. It is therefore indicated that for this indication the compound of Example 2 may be administered orally at daily dosages of from 1400 mg to 2100 mg to larger mammals, for example humans.

The present invention also provides pharmaceutical compostions containing a compound according to the invention in association with at least one pharmaceutical carrier or diluent. Such composition may be manufactured in conventional manner. Unit dosage forms contain, for example, from about 20 mg to about 1500 mg of a compound according to the invention.

The following Examples, in which all temperatures are in degrees centigrade, illustrate the invention:

EXAMPLE 1

Culture of strain NRRL 18230 in Erlenmeyer flask

Starting cultures of the strain NRRL 18230 are incubated at 21° for 14 days on MA in slants. A preculture is then produced by homogenising the complete contents of one starting culture under sterile conditions, transfering to a 500 ml Erlenmeyer flask containing 200 ml nutrient solution M (2% malt extract, 0.4% yeast extract in demineralized water), and incubating on a rotating shaker at 200 rpm for 10 days at 21°.

Intermediate cultures are then obtained by transferring 20 ml of the preculture to a 500 ml Erlenmeyer flask containing 200 ml of nutrient solution M and incubating on a rotary shaker at 200 rpm for 7 days at 21°.

Finally for a production culture, 100 Erlenmeyer flasks (500 ml) each containing 200 ml of nutrient solution M are each inocculated with 20 ml of the intermediate cultures. The flasks are incubated at 21° in a rotary shaker at 200 rpm. After 10 days the 20 liters of fermentation broth are combined for the extraction of the product.

EXAMPLE 2

Isolation of (Thr)² (Leu)⁵ (D-Hiv)⁸ (Leu)¹⁰-Ciclosporin

The 20 liters of culture medium obtained from Example 1 are subjected to high-shear mixing in a rod mixer (Lutz, Wertheim, Germany) to break up the cells, then extracted three times with 20 liters of ethyl acetate. The 60 liters of organic phase are combined, dried over anhydrous sodium sulphate and evaporated to dryness under vacuum, giving a residue of 17.4 g.

The residue is dissolved in 80 ml methanol and chromatographed on a 90 mm diameter column containing 1300 g SEPHADEX LH-20 (Pharmacia Fine Chemicals AB, Uppsala, Sweden). Fractions of 100 ml are taken, whereby (Thr)² (Leu)⁵ (D-Hiv)⁸ (Leu)¹⁰-Ciclosporin appears in fractions 22-30. These are combined and evaporated under vacuum to give 8400 mg of a light coloured solid foam. This residue is dissolved in wet ethyl acetate and chromatographed on a 55 mm diameter column containing 500 g KIESELGEL (Merck) of particle size 0.04-0.063 mm. The desired product is detected in fractions 9-14 (100 ml fraction size). Evaporation gives a pale yellow residue (4200 mg). Treatment with decolorizing charcoal (Merck) in diethyl ether and filtration through a thin layer of talc gives (Thr)² (Leu)⁵ (D-Hiv)⁸ (Leu)¹⁰-Ciclosporin as a white powder, recrystallized from ether m.p. 163°-164° (decomp.); $[\alpha]_D^{20} = -186°$, (c=1 in MeOH); $[\alpha]_D^{20} = -223°$ (c=1 in CHCl₃).

EXAMPLES 3-7

By modification of the above chromatographic techniques, the following compounds may be isolated in minor amounts from the production fermentation broth:

| Ex. No. | Compound |
|---|---|
| 3 | (Thr)² (D-Hiv)⁸ (Leu)¹⁰-Ciclosporin |
| 4 | (Thr)² (Ile)⁵ (D-Hiv)⁸ (Leu)¹⁰-Ciclosporin |
| 5 | (Thr)² (Leu)⁴ (Leu)⁵ (D-Hiv)⁸ (Leu)¹⁰-Ciclosporin |
| 6 | (Thr)² (Gly)³ (Leu)⁵ (D-Hiv)⁸ (Leu)¹⁰-Ciclosporin |
| 7 | (8'-OHMeBmt)¹ (Thr)² (Leu)⁵ (D-Hiv)⁸ (Leu)¹⁰-Ciclosporin |

The compounds have the properties shown in Table I:

TABLE I

| Compound of Ex. No. | formula | MW calc | MW found* | mp °C. | $[\alpha]_D^{20}$ (c = 1 in MeOH) |
|---|---|---|---|---|---|
| 3 | C₆₃H₁₁₂N₁₀O₁₄ | 1233.6 | 1233.9 | 164 (dec) | −184° |
| 4 | C₆₄H₁₁₄N₁₀O₁₄ | 1247.7 | 1247.6 | 151-153 (dec) | −180° |
| 5 | C₆₃H₁₁₂N₁₀O₁₄ | 1233.6 | 1233.6 | 166-168 (dec) | −174° |
| 6 | C₆₃H₁₁₂N₁₀O₁₄ | 1233.6 | 1233.6 | 140-143 (dec) | −154° |
| 7 | C₆₄H₁₄₄N₁₀O₁₅ | 1263.7 | 1263 | 158 (sinters) 195 (dec) | −174° |

*by FAB (Fast Atomic Bombardment) mass spectrometry

Thin Layer Chromatography
Thin layer plates Merck: Silica gel
Carrier system: CH₂Cl₂-7% CH₃OH
Length of run: 120 mm
Colouring with iodine vapour

| Example | Rf value |
|---|---|
| 2 | 0.358 |
| 3 | 0.308 |
| 4 | 0.337 |
| 5 | 0.263 |
| 6 | 0.242 |
| 7 | 0.179 |

EXAMPLE 8

Synthesis of (Thr)² (Leu)⁵ (D-Hiv)⁸ (Leu)¹⁰-Ciclosporin by cyclisation

At room temperature, 2.4 g (2.29 mmol) of the unprotected hydroxy-undecapeptide

HO-(D)Hiv-MeLeu-Leu-MeVal-MeBmt-Thr-Sar-MeLeu-Leu-MeLeu-Ala-OH.

0.84 g (6.88 mmol) of 4-dimethylaminopyridine and 0.66 g (1.5 equiv, 3.44 mmol) of N-ethyl-N-(3-dimethylamino)propyl carbodiimide are dissolved in 145 ml methylene chloride and reacted for three days with stirring and exclusion of moisture. The resulting solution is diluted with 300 ml of methylene chlorde, shaken with 100 ml of water acifified to pH 2 with 1N HCl, filtered through talc and evaporated. The residue is chromatographed on 100 g of silica gel using 10% MeOH/CH₂Cl₂, to give the title compound (2.55 g, 89%). Identity with the compound of Example 2 is established by NMR spectroscopy and $[\alpha]_D^{20}$ (−220°, c=1 in CHCl₃).

TABLE II

| Abbreviations | |
|---|---|
| Abu | α-aminobutyric acid |
| Ala | alanine |
| BOC | t-butyloxycarbonyl |
| Bz | benzyl |
| Gly | glycine |
| Hiv | α-hydroxyisovaleric acid |
| Ile | isoleucine |
| Leu | leucine |
| MeBmt | N-methyl-(4R)-4-but-2E-en-1-yl-4-methyl-(L)-threonine |
| MeBmtH₂ | N-methyl-(4R)-4-but-1-yl-4-methyl-(L)-threonine |
| 8'-OHMeBmt | N-methyl-(4R)-4-(4'-hydroxybut-2E-en-1-yl)-4-methyl-(L)-threonine |
| Sar | sarcosine |
| Thr | threonine |
| Val | valine |

We claim:

1. A cyclosporin of formula II

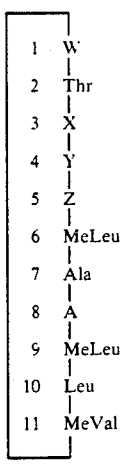

in which

W is MeBmt, 8'-OHMeBmt, or MeBmtH₂,

X is Sar or Gly,
Y is MeLeu or Leu,
Z is Leu, Ile or Val, and
A is a group of formula III $$-O-\underset{\underset{R}{|}}{CH}-CO-$$

in which R is $C_{1-4}$ alkyl.

2. A cyclosporin according to claim 1 in which R is isopropyl.

3. (Thr)² (Leu)⁵ (D-Hiv)⁸ (Leu)¹⁰-Ciclosporin.
4. (Thr)² (D-Hiv)⁸ (Leu)¹⁰-Ciclosporin.
5. (Thr)² (Ile)⁵ (D-Hiv)⁸ (Leu)¹⁰-Ciclosporin.
6. (Thr)² (Leu)⁴ (Leu)⁵ (D-Hiv)⁸ (Leu)¹⁰-Ciclosporin.
7. (Thr)² (Gly)³ (Leu)⁵ (D-Hiv)⁸ (Leu)¹⁰-Ciclosporin.
8. (8'-OH MeBmt)¹ (Thr)² (Leu)⁵ (D-Hiv)⁸ (Leu)¹⁰-Ciclosporin.

9. A pharmaceutical composition comprising a therapeutically effective amount of a cyclosporin according to claim 1 and a pharmaceutically acceptable carrier therefor.

* * * * *